United States Patent
Lee et al.

(10) Patent No.: US 11,590,303 B2
(45) Date of Patent: Feb. 28, 2023

(54) AEROSOL GENERATING DEVICE HAVING A FIRST HEATER AND A SECOND HEATER, AND A METHOD OF CONTROLLING THE POWER OF THE FIRST AND SECOND HEATERS IN THE AEROSOL GENERATING DEVICE

(71) Applicant: KT&G CORPORATION, Daejeon (KR)

(72) Inventors: Jae Min Lee, Siheung-si (KR); Hyung Jin Jung, Seoul (KR)

(73) Assignee: KT&G CORPORATION, Daejeon (KR)

( * ) Notice: Subject to any disclaimer, the term of this patent is extended or adjusted under 35 U.S.C. 154(b) by 192 days.

(21) Appl. No.: 16/959,296

(22) PCT Filed: Oct. 23, 2019

(86) PCT No.: PCT/KR2019/014003
§ 371 (c)(1),
(2) Date: Jun. 30, 2020

(87) PCT Pub. No.: WO2020/101206
PCT Pub. Date: May 22, 2020

(65) Prior Publication Data
US 2020/0368462 A1    Nov. 26, 2020

(30) Foreign Application Priority Data
Nov. 16, 2018    (KR) .......................... 10-2018-0141969

(51) Int. Cl.
*A24B 15/167*    (2020.01)
*A61M 15/06*    (2006.01)
(Continued)

(52) U.S. Cl.
CPC ........... *A61M 15/06* (2013.01); *A24B 15/167* (2016.11); *A61M 11/042* (2014.02);
(Continued)

(58) Field of Classification Search
CPC .... H05B 1/02; H05B 2203/021; A61M 15/06; A61M 11/042; A24B 15/167
(Continued)

(56) References Cited

U.S. PATENT DOCUMENTS

| 7,726,320 B2 * | 6/2010 | Robinson | ............... A24B 15/12 |
| | | | 131/194 |
| 8,910,639 B2 * | 12/2014 | Chang | .................... H01R 43/26 |
| | | | 131/225 |

(Continued)

FOREIGN PATENT DOCUMENTS

| CN | 104994757 A | 10/2015 |
| CN | 108783602 A | 11/2018 |

(Continued)

OTHER PUBLICATIONS

Notification of Reason for Refusal dated Jun. 9, 2020 from the Korean Intellectual Property Office in KR Application No. 10-2018-0141969.

(Continued)

*Primary Examiner* — Abdullah A Riyami
*Assistant Examiner* — Vladimir Imas
(74) *Attorney, Agent, or Firm* — Sughrue Mion, PLLC

(57) ABSTRACT

An embodiment of the present disclosure, may provide an aerosol generating device which may include a first heater for heating a cigarette inserted into a first portion of the aerosol generating device; a second heater for heating a liquid composition stored in a cartridge detachably attached to a second portion of the aerosol generating device; and a controller for controlling power supplied to the first heater (Continued)

and the second heater, wherein the controller may control the power supplied to the second heater based on a heating pattern by which the first heater is heated.

20 Claims, 9 Drawing Sheets

(51) Int. Cl.
    *A61M 11/04*         (2006.01)
    *H05B 1/02*         (2006.01)

(52) U.S. Cl.
    CPC ....... *A61M 2205/8206* (2013.01); *H05B 1/02* (2013.01); *H05B 2203/021* (2013.01)

(58) Field of Classification Search
    USPC .......................................................... 131/329
    See application file for complete search history.

(56) References Cited

U.S. PATENT DOCUMENTS

| | | | |
|---|---|---|---|
| 8,910,640 B2 * | 12/2014 | Sears | F22B 1/28 131/194 |
| 9,067,029 B2 | 6/2015 | Yamada et al. | |
| 9,277,770 B2 * | 3/2016 | DePiano | A24F 40/46 |
| 9,609,893 B2 * | 4/2017 | Novak, III | A61M 15/06 |
| 9,806,549 B2 * | 10/2017 | Liberti | A24F 40/00 |
| 9,955,726 B2 * | 5/2018 | Brinkley | A24F 40/42 |
| 10,143,236 B2 * | 12/2018 | DePiano | A24F 40/70 |
| 10,206,429 B2 * | 2/2019 | Davis | A24F 40/46 |
| 10,258,089 B2 * | 4/2019 | Sears | A24F 40/44 |
| 10,595,561 B2 * | 3/2020 | DePiano | A24F 40/40 |
| 10,609,961 B2 * | 4/2020 | Ampolini | H01C 3/08 |
| 11,202,343 B2 * | 12/2021 | Nakano | B05B 12/082 |
| 11,234,463 B2 * | 2/2022 | DePiano | F22B 1/282 |
| 11,246,998 B2 | 2/2022 | Greim | |
| 11,317,476 B2 * | 4/2022 | Schmidt | A24F 40/44 |
| 2014/0338686 A1 * | 11/2014 | Plojoux | A24F 40/485 131/329 |
| 2016/0374397 A1 | 12/2016 | Jordan et al. | |
| 2017/0238610 A1 | 8/2017 | Reevell | |
| 2019/0297951 A1 | 10/2019 | Kuczaj | |
| 2019/0380389 A1 | 12/2019 | Hong et al. | |
| 2020/0086068 A1 | 3/2020 | Lee et al. | |

FOREIGN PATENT DOCUMENTS

| | | |
|---|---|---|
| EP | 3 066 942 A1 | 9/2016 |
| EP | 2 967 138 B1 | 11/2017 |
| JP | 2010-506594 A | 3/2010 |
| KR | 10-1076144 B1 | 10/2011 |
| KR | 10-2015-0102924 A | 9/2015 |
| KR | 10-2018-0085365 A | 7/2018 |
| KR | 10-2018-0111460 A | 10/2018 |
| KR | 10-2018-0115681 A | 10/2018 |
| WO | 2008/108889 A1 | 9/2008 |
| WO | 2018/019855 A1 | 2/2018 |

OTHER PUBLICATIONS

International Search Report for PCT/KR2019/014003 dated Jan. 29, 2020 [PCT/ISA/210].

Extended European Search Report dated Feb. 17, 2022 in European Application No. 19885099.2.

Office Action dated Dec. 20, 2022 in CN Patent Application No. 201980006441.3.

\* cited by examiner

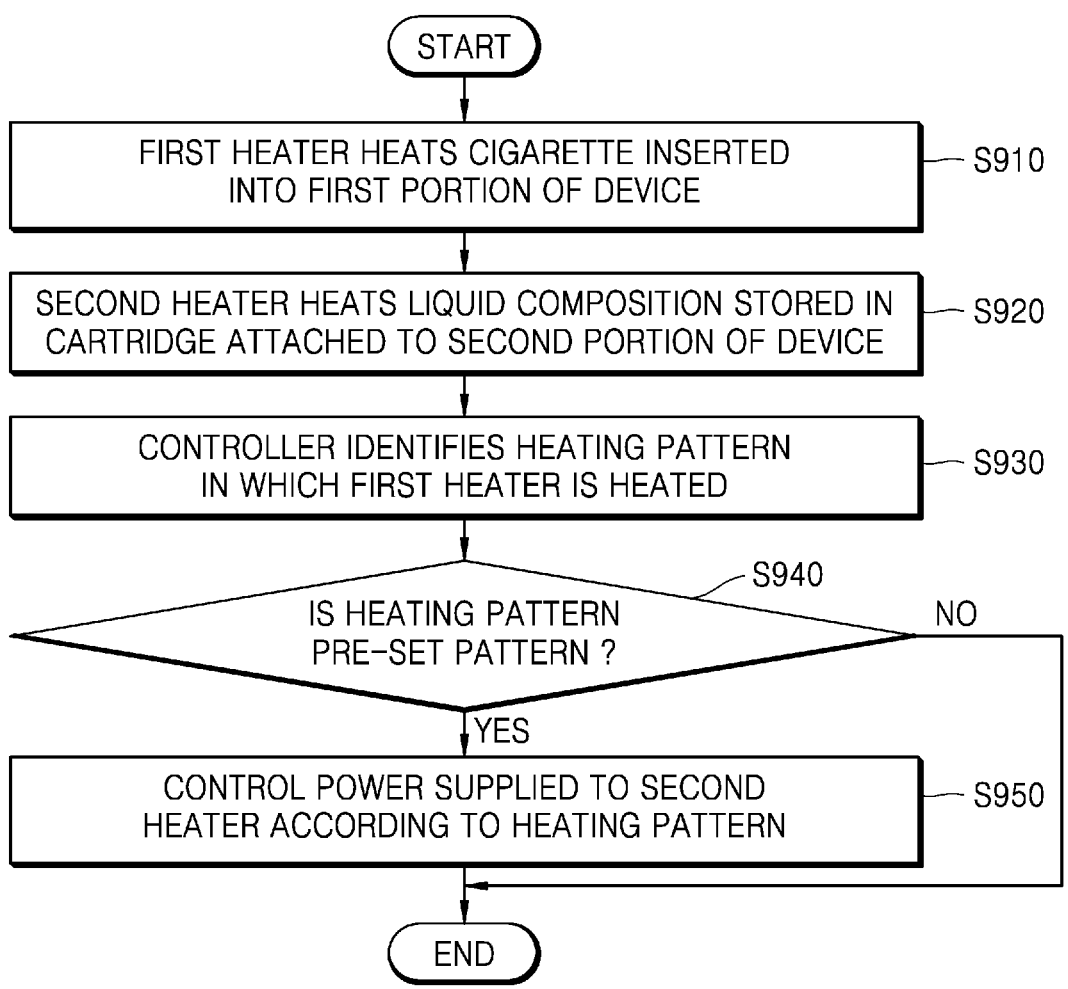

AEROSOL GENERATING DEVICE HAVING A FIRST HEATER AND A SECOND HEATER, AND A METHOD OF CONTROLLING THE POWER OF THE FIRST AND SECOND HEATERS IN THE AEROSOL GENERATING DEVICE

CROSS REFERENCE TO RELATED APPLICATIONS

This application is a National Stage of International Application No. PCT/KR2019/014003 filed Oct. 23, 2019, claiming priority based on Korean Patent Application No. 10-2018-0141969 filed Nov. 16, 2018.

TECHNICAL FIELD

The present disclosure relates to an aerosol generating device having a first heater and a second heater, and a method of controlling the power of the first and second heaters in the aerosol generating device, and more particularly to a method of effectively controlling the power supplied to a first heater and a second heater provided in an aerosol generating device, and the aerosol generating device in which the method is implemented.

BACKGROUND ART

Recently, there has been increasing demand for alternative ways of overcoming the disadvantages of traditional cigarettes. For example, there is growing demand for a method of generating aerosol by heating an aerosol generating material in cigarettes, rather than by combusting cigarettes. Accordingly, research into a heating-type cigarette or a heating-type aerosol generator has been actively conducted.

When a plurality of heaters are included in the aerosol generating device, the heater that is heated first influences the heater that is subsequently heated. For example, in the case where there are two heaters in the aerosol generating device, when the first heater is heated and then the second heater is heated, the temperature of the aerosol generating device rises as the first heater is heated. Therefore, the heating start temperature of the second heater becomes higher than room temperature by the temperature increase of the aerosol generating device. In this state, when the second heater is heated, sufficient heat energy is not applied to the aerosol generating substrate for generating an aerosol, and thus a sufficient amount of vapor may not be generated.

DESCRIPTION OF EMBODIMENTS

Technical Problem

Technical problems to be solved by the present disclosure are to provide a method of effectively controlling the power supplied to a first heater and a second heater in the aerosol generating device having the first heater and the second heater, and an aerosol generating device operated by the method.

Solution to Problem

An aerosol generating device according to an embodiment of the present disclosure for solving the above technical problem, may include a first heater for heating a cigarette inserted into a first portion of the aerosol generating device; a second heater for heating a liquid composition stored in a cartridge that is detachably attached to a second portion of the aerosol generating device; and a controller for controlling power supplied to the first heater and the second heater, wherein the controller may control the power supplied to the second heater based on a heating pattern by which the first heater is heated.

A method of controlling a first heater and a second heater of the aerosol generating device according to another embodiment of the present disclosure for solving the above technical problem, may include heating, by the first heater, a cigarette inserted into a first portion of the aerosol generating device; heating, by the second heater, a liquid composition stored in a cartridge detachably attached to a second portion of the aerosol-generating device; and controlling, by a controller, power supplied to the second heater based on a heating pattern in which the first heater is heated.

In addition, a cigarette or an aerosol generating device using the cigarette according to still other embodiment of the present disclosure, may be provided to a user to solve the above technical problem.

Advantageous Effects of Disclosure

According to the present disclosure, the power supplied to a first heater and a second heater provided in the aerosol generating device may be effectively controlled, thereby preventing a shortage of an amount of vapor due to uneven heating.

BRIEF DESCRIPTION OF DRAWINGS

FIG. 9 is a flowchart illustrating an example of a method of controlling the power of a first heater and a second heater in an aerosol generating device according to the present disclosure.

BEST MODE

Figure 1:
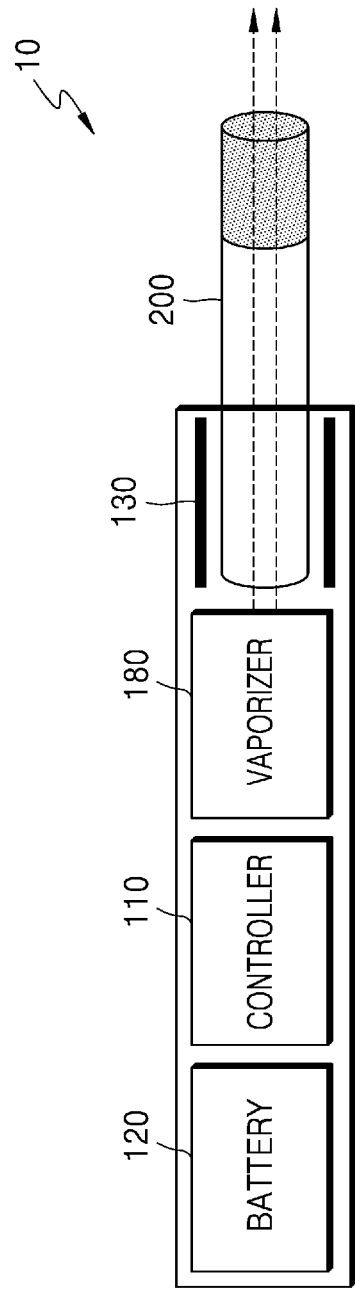
FIGS. 1 and 2 are diagrams showing examples in which a cigarette is inserted into an aerosol generating device.

Device according to an embodiment of the present disclosure for solving the above technical problem, may include a first heater for heating a cigarette inserted into a first portion of the aerosol generating device; a second heater for heating a liquid composition stored in a cartridge that is detachably attached to a second portion of the aerosol generating device; and a controller for controlling power supplied to the first heater and the second heater, wherein the controller may control the power supplied to the second heater based on a heating pattern by which the first heater is heated.

In the device, the heating pattern may indicate that the first heater reaches a pre-set preheating temperature and maintains the preheating temperature for a pre-set period of time.

In the device, the heating pattern may indicate that an internal temperature of the aerosol generating device measured by a temperature sensor exceeds a pre-set value as the first heater maintains the preheating temperature for the pre-set period of time.

In the device, the heating pattern may indicate that an internal temperature of the aerosol generating device exceeds a pre-set value after the first heater reaches a pre-set preheating temperature, and the controller may control reduce power supplied to the second heater based on the heating pattern.

In the device, the internal temperature of the aerosol generating device may be measured by a temperature sensor attached to a cartridge.

In the device, the internal temperature of the aerosol generating device may be obtained by referring to a table showing different periods of time and different temperatures of the aerosol generating device which respectively correspond to the different periods of time.

In the device, the controller may increase power supplied to the second heater based on heat energy transferred to a cigarette when a pre-set preheating temperature is maintained for a pre-set period of time after the first heater reaches the pre-set preheating temperature.

In the device, the controller may reduce the power supplied to the second heater in proportion to a rise of an internal temperature of the aerosol generating device when the first heater reaches a pre-set preheating temperature.

In the device, the controller may increase the reduced power supplied to the second heater based on heat energy transferred to a cigarette.

In the device, the controller may store a temperature profile corresponding to the heating pattern, and control power supplied to the second heater according to the stored temperature profile.

An method of controlling power of a first heater and a second heater in an aerosol generating device according to an embodiment of the present disclosure for solving the above technical problem may include heating, by the first heater, a cigarette inserted into a first portion of the aerosol generating device; heating, by the second heater, a liquid composition stored in a cartridge detachably attached to a second portion of the aerosol-generating device; and controlling, by a controller, power supplied to the second heater based on a heating pattern by which the first heater is heated.

In the method, the heating pattern may indicate that the first heater reaches a pre-set preheating temperature and maintains the preheating temperature for a pre-set period of time.

In the method, the heating pattern may indicate that an internal temperature of the aerosol generating device measured by a temperature sensor exceeds a pre-set value as the first heater maintains the preheating temperature for the pre-set period of time.

In the method, the heating pattern may indicate that an internal temperature of the aerosol generating device exceeds a pre-set value after the first heater reaches a pre-set preheating temperature, and the controlling may include reducing the power supplied to the second heater based on the heating pattern.

In the method, the internal temperature of the aerosol generating device may be measured by a temperature sensor attached to the cartridge.

In the method, the internal temperature of the aerosol generating device may be obtained by referring to a table showing different periods of time for maintaining the pre-set preheating temperature and different temperatures of the aerosol generating device which respectively correspond to the different periods of time.

In the method, the controlling may include increasing power supplied to the second heater based on heat energy transferred to a cigarette when a pre-set preheating temperature is maintained for a pre-set period of time after the first heater reaches the pre-set preheating temperature.

In the method, the controlling may include reducing power supplied to the second heater in proportion to a rise of an internal temperature of the aerosol generating device when the first heater reaches a pre-set preheating temperature.

In the method, the controlling may include increasing the reduced power supplied to the second heater based on heat energy transferred to a cigarette.

In the method, the controlling may include storing a temperature profile corresponding to the heating pattern, and controlling power supplied to the second heater according to the stored temperature profile.

Mode of Disclosure

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

The example embodiments will be described below in more detail with reference to the accompanying drawings.

Figure 2:
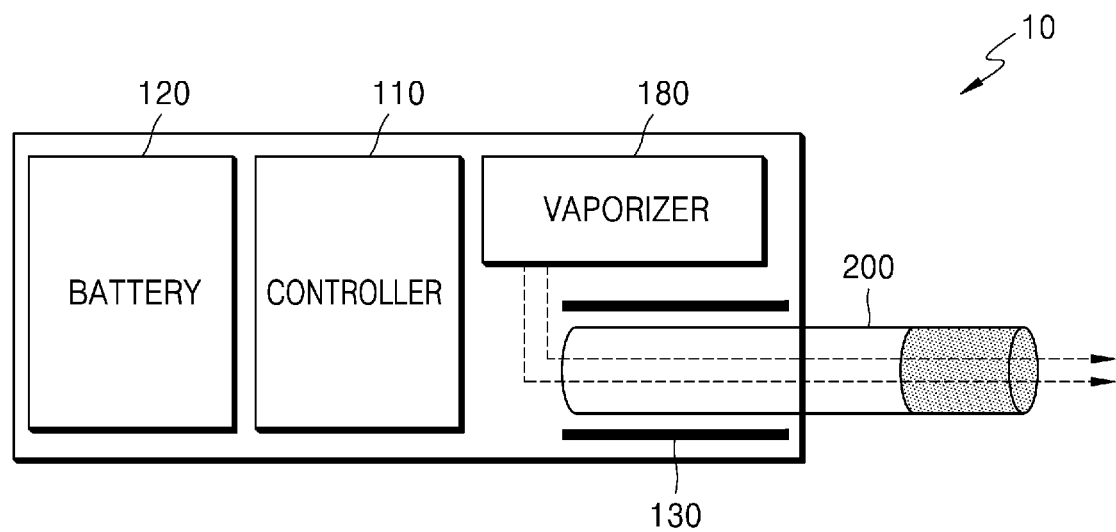

FIGS. 1 and 2 are diagrams showing examples in which a cigarette is inserted into an aerosol generating device.

Referring to FIG. 1 and FIG. 2, an aerosol generator 10 includes a battery 120, a controller 110, and a heater 130 and a vaporizer 180. Also, a cigarette 200 may be inserted into an inner space of the aerosol generator 10.

The elements related to the embodiment are illustrated in the aerosol generator 10 of FIGS. 1 to 2. Therefore, one of ordinary skill in the art would appreciate that other universal elements than the elements shown in FIGS. 1 to 2 may be further included in the aerosol generator 10.

Also, FIGS. 1 and 2 show that the aerosol generator 10 includes the heater 130, but if necessary, the heater 130 may be omitted.

FIG. 1 shows that the battery 120, the controller 110, the vaporizer 180, and the heater 130 are arranged in a row. Also, FIG. 2 shows that the vaporizer 180 and the heater 130 are arranged in parallel. However, an internal structure of the aerosol generator 10 is not limited to the examples shown in FIGS. 1 to 2. That is, according to a design of the aerosol generator 10, arrangement of the battery 120, the controller 110, the heater 130, and the vaporizer 180 may be changed.

When the cigarette 200 is inserted into the aerosol generator 10, the aerosol generator 10 operates the heater 130 and/or the vaporizer 180 to generate aerosol from the cigarette 200 and/or the vaporizer 180. The aerosol generated by the heater 130 and/or the vaporizer 180 may be transferred to a user via the cigarette 200. If necessary, even when the cigarette 200 is not inserted in the aerosol generator 10, the aerosol generator 10 may heat the heater 130.

The battery 120 supplies the electric power used to operate the aerosol generator 10. For example, the battery 120 may supply power for heating the heater 130 or the vaporizer 180 and supply power for operating the controller 110. In addition, the battery 120 may supply power for operating a display, a sensor, a motor, and the like installed in the aerosol generator 10.

The controller 110 controls the overall operation of the aerosol generator 10. In detail, the controller 110 may control operations of other elements included in the aerosol generator 10, as well as the battery 120, the heater 130, and the vaporizer 180. Also, the controller 110 may check the status of each component in the aerosol generator 10 to determine whether the aerosol generator 10 is in an operable state.

The controller 110 includes at least one processor. A processor can be implemented as an array of a plurality of logic gates or can be implemented as a combination of a general-purpose microprocessor and a memory in which a program executable in the microprocessor is stored. It will be understood by one of ordinary skill in the art that the present disclosure may be implemented in other forms of hardware.

The heater 130 may be heated by the electric power supplied from the battery 120. For example, when the cigarette is inserted in the aerosol generator 10, the heater 130 may be located outside the cigarette Therefore, the heated heater 130 may raise the temperature of an aerosol generating material in the cigarette.

The heater 130 may be an electro-resistive heater. For example, the heater 130 includes an electrically conductive track, and the heater 130 may be heated as a current flows through the electrically conductive track. However, the heater 130 is not limited to the above example, and any type of heater may be used provided that the heater is capable of being heated to a desired temperature. Here, the desired temperature may be set in advance on the aerosol generator 10, or may be set by a user.

In addition, in another example, the heater 130 may include an induction heating type heater. In detail, the heater 130 may include an electrically conductive coil for heating the cigarette in an induction heating method, and the cigarette may include a susceptor that may be heated by the induction heating type heater.

Referring to FIGS. 1 and 2, the heater 130 is illustrated as being disposed outside the cigarette 200, but is not limited thereto. For example, the heater may include a tubular type heating element, a plate type heating element, a needle type heating element, or a rod type heating element, and may heat the inside or outside of the cigarette 200 according to the shape of the heating element.

Also, there may be a plurality of heaters 130 in the aerosol generator 10. Here, the plurality of heaters 130 may be arranged to be inserted into the cigarette 200 or on the outside of the cigarette 200. Also, some of the plurality of heaters 130 may be arranged to be inserted into the cigarette 200 and the other may be arranged on the outside of the cigarette 200. In addition, the shape of the heater 130 is not limited to the example shown in FIGS. 1 to 2, but may be manufactured in various shapes.

The vaporizer 180 may generate aerosol by heating a liquid composition and the generated aerosol may be delivered to the user after passing through the cigarette 200. In other words, the aerosol generated by the vaporizer 180 may move along an air flow passage of the aerosol generator 10, and the air flow passage may be configured for the aerosol generated by the vaporizer 180 to be delivered to the user through the cigarette For example, the vaporizer 180 may include a liquid storage unit, a liquid delivering unit, and a heating element, but is not limited thereto. For example, the liquid storage unit, the liquid delivering unit, and the heating element may be included in the aerosol generator 10 as independent modules.

The liquid storage may store a liquid composition. For example, the liquid composition may be a liquid including a tobacco containing material including a volatile tobacco flavor component, or a liquid including a non-tobacco material. The liquid storage unit may be detachable from the vaporizer 180 or may be integrally manufactured with the vaporizer 180.

For example, the liquid composition may include water, solvents, ethanol, plant extracts, flavorings, flavoring agents, or vitamin mixtures. The flavoring may include, but is not limited to, menthol, peppermint, spearmint oil, various fruit flavoring ingredients, etc. The flavoring agent may include components that may provide the user with various flavors or tastes. Vitamin mixtures may be a mixture of at least one of vitamin A, vitamin B, vitamin C, and vitamin E, but are not limited thereto. Also, the liquid composition may include an aerosol former such as glycerin and propylene glycol.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

The heating element is an element for heating the liquid composition delivered by the liquid delivering unit. For example, the heating element may be a metal heating wire, a metal hot plate, a ceramic heater, or the like, but is not limited thereto. In addition, the heating element may include a conductive filament such as nichrome wire and may be positioned as being wound around the liquid delivery element. The heating element may be heated by a current supply and may transfer heat to the liquid composition in contact with the heating element, thereby heating the liquid composition. As a result, aerosol may be generated.

For example, the vaporizer 180 may be referred to as a cartomizer or an atomizer, but is not limited thereto.

In addition, the aerosol generator 10 may further include universal elements, in addition to the battery 120, the controller 110, the heater 130, and the vaporizer 180. For example, the aerosol generator 10 may include a display capable of outputting visual information and/or a motor for outputting tactile information. In addition, the aerosol generator 10 may include at least one sensor (a puff sensor, a temperature sensor, a cigarette insertion sensor, etc.) Also, the aerosol generator 10 may be manufactured to have a structure, in which external air may be introduced or internal air may be discharged even in a state where the cigarette 200 is inserted.

Although not shown in FIGS. 1 to 2, the aerosol generator 10 may configure a system with an additional cradle. For example, the cradle may be used to charge the battery 120 of the aerosol generator 10. Alternatively, the heater 130 may be heated while the cradle and the aerosol generator 10 are coupled to each other.

The cigarette 200 may be similar to a traditional combustive cigarette. For example, the cigarette 200 may include a first portion containing an aerosol generating material and a second portion including a filter and the like. The second portion of the cigarette 200 may also include the aerosol generating material. For example, an aerosol generating material made in the form of granules or capsules may be inserted into the second portion.

The entire first portion may be inserted into the aerosol generator 10 and the second portion may be exposed to the outside. Alternatively, only a portion of the first portion may be inserted into the aerosol generator 10 or the entire first portion and a portion of the second portion may be inserted into the aerosol generator 10. The user may puff aerosol while holding the second portion by the mouth of the user. At this time, the aerosol is generated as the outside air passes through the first portion, and the generated aerosol passes through the second portion and is delivered to a user's mouth.

For example, the outside air may be introduced through at least one air passage formed in the aerosol generator 10. For example, opening and closing of the air passage formed in the aerosol generator 10 and/or the size of the air passage may be adjusted by a user. Accordingly, the amount and smoothness of vapor may be adjusted by the user. In another example, the outside air may be introduced into the cigarette 200 through at least one hole formed in a surface of the cigarette 200.

Hereinafter, an example of the cigarette 200 will be described with reference to FIG. 3.

Figure 3:
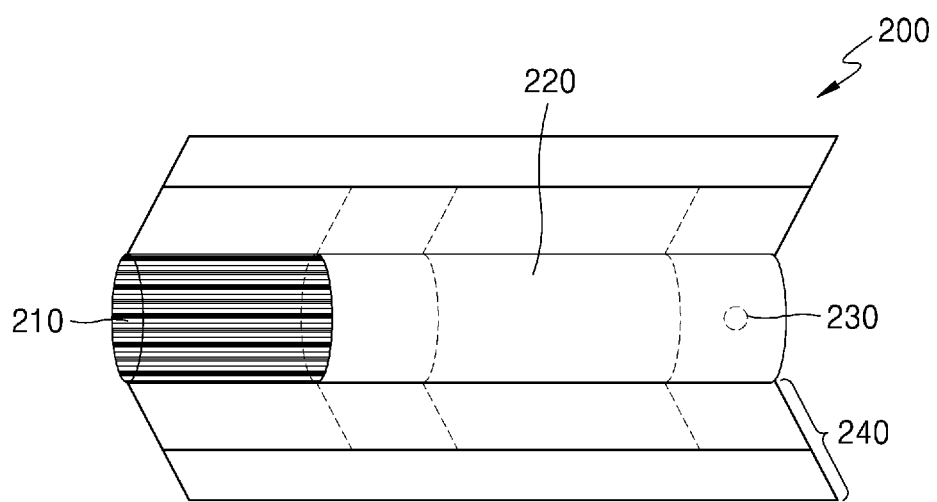
FIGS. 3 and 4 are diagrams showing examples of cigarettes.

FIG. 3 illustrates an example of a cigarette.

Referring to FIG. 3, the cigarette 200 includes a tobacco rod 210 and a filter rod 220. The first portion described above with reference to FIGS. 1 to 2 may include the tobacco rod 210 and the second portion may include the filter rod 220.

In FIG. 3, the filter rod 220 is shown as a single segment, but is not limited thereto. In other words, the filter rod 220 may include a plurality of segments. For example, the filter rod 220 may include a first segment for cooling down the aerosol and a second segment for filtering a predetermined component included in the aerosol. Also, if necessary, the filter rod 220 may further include at least one segment performing other functions.

The diameter of the cigarette 200 is within the range of 5 mm to 9 mm, and the length may be about 48 mm. However, embodiments are not limited thereto. For example, the length of the tobacco rod 210 may be about 12 mm, the length of the first segment of the filter rod 220 may be about 10 mm, the second segment of the filter rod 220 may be about 14 mm, and the third segment of the filter rod 220 may be about 12 mm. However, it is not limited thereto.

For example, the cigarette 200 may be packaged by one wrapper 240. The wrapper 240 may include at least one hole through which the outside air is introduced or inside air is discharged. For example, the cigarette 200 may be packaged by one wrapper 240. In another example, the cigarette 200 may be packaged by two or more wrappers 240. For example, the tobacco rod 210 may be packaged by a first wrapper, and the filter rod 220 may be packaged by a second wrapper. In addition, the tobacco rod 210 and the filter 220 that are respectively packaged by single wrappers, and then, the cigarette 200 may be entirely re-packaged by a third wrapper. When the tobacco rod 210 or filter rod 220 include a plurality of segments, each segment may be packaged via a separate wrapper, and the segments of the cigarette 200 may be re-packaged by another wrapper.

The tobacco rod 210 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. In addition, the tobacco rod 210 may include other additive materials like a flavoring agent, a wetting agent, and/or an organic acid. Also, a flavoring liquid such as menthol, humectant, etc. may be added to the tobacco rod 210 by being sprayed to the tobacco rod 210.

The tobacco rod 210 may be manufactured variously. For example, the tobacco rod 210 may be fabricated as a sheet or a strand. Also, the tobacco rod 210 may be fabricated by tobacco leaves that are obtained by fine-cutting a tobacco sheet. Also, the tobacco rod 210 may be surrounded by a heat conducting material. For example, the heat-conducting material may be, but is not limited to, a metal foil such as aluminum foil. For example, the heat conducting material surrounding the tobacco rod 210 may improve a thermal conductivity applied to the tobacco rod by evenly dispersing the heat transferred to the tobacco rod 210, and thereby improving tobacco taste. Also, the heat conducting material surrounding the tobacco rod 210 may function as a susceptor that is heated by an inducting heating type heater. Although not shown in the drawings, the tobacco rod 210 may further include a susceptor, in addition to the heat conducting material surrounding the outside thereof.

The filter rod 220 may be a cellulose acetate filter. In addition, the filter rod 220 is not limited to a particular shape. For example, the filter rod 220 may be a cylinder type rod or a tube type rod including a cavity therein. Also, the filter rod 220 may be a recess type rod. When the filter rod 220 includes a plurality of segments, at least one of the plurality of segments may have a different shape from the others.

Also, the filter rod 220 may include at least one capsule 230. Here, the capsule 230 may generate flavor or may generate aerosol. For example, the capsule 230 may have a structure, in which a liquid containing a flavoring material is wrapped with a film. The capsule 230 may have a circular or cylindrical shape, but is not limited thereto.

Referring to 4, the cigarette 3 may further include the front-end plug 33 The front-end plug 33 may be located on a side of the tobacco rod 31, the side not facing the filter rod 32. The front-end plug 33 may prevent the tobacco rod 31 from escaping to the outside and may prevent liquefied aerosol from flowing from the tobacco rod 31 into an aerosol generating device (1 of FIGS. 1 to 3) during smoking.

The filter rod 32 may include a first segment 321 and a second segment 322. Here, the first segment 321 may correspond to the first segment of the filter rod 220 of FIG. 3, and the second segment 322 may correspond to the third segment of the filter rod 220 of FIG. 3.

The diameter and the total length of the cigarette 3 may correspond to the diameter and the total length of the cigarette 200 in FIG. 3. For example, the length of the front-end plug 33 may be about 7 mm, the length of the cigarette rod 31 may be about 15 mm, the length of the first segment 321 may be about 12 mm, and the length of the second segment 322 may be about 14 mm. However, embodiments are not limited thereto.

The cigarette 3 may be packaged by at least one wrapper 35. The wrapper 35 may have at least one hole through which external air may be introduced or internal air may be discharged. For example, the front-end plug 33 is packaged by a first wrapper 351, the cigarette rod 31 is packaged by a second wrapper 352, the first segment 321 may be packaged by a third wrapper 353, and the second segment 322 may be packaged by a fourth wrapper 354. And the entire cigarette 3 may be repackaged by a fifth wrapper 355.

In addition, at least one perforation 36 may be formed in the fifth wrapper 355. For example, the perforation 36 may be formed in an area surrounding the cigarette rod 31, but is not limited thereto. The perforation 36 may serve to transfer the heat formed by the heater 130 shown in FIGS. 1 and 2 to the inside of the cigarette rod 31.

Also, at least one capsule 34 may be included in the second segment 322. Here, the capsule 34 may generate a flavor or aerosol. For example, the capsule 34 may have a configuration in which a liquid containing a flavoring material is wrapped with a film. For example, the capsule 34 may have a spherical or cylindrical shape, but is not limited thereto.

The first wrapper 351 may be a metal foil such as aluminum foil bonded to a general filter wrapping paper. For example, the total thickness of the first wrapper 351 may be in the range of 45 um to 55 um, and preferably 50.3 um. In addition, the thickness of the metal foil of the first wrapper 351 may be in the range of 6 um to 7 um, and preferably 6.3 um. In addition, the basis weight of the first wrapper 351 may be in the range of 50 $g/m^2$ to 55 $g/m^2$, and preferably 53 $g/m^2$.

The second wrapper 352 and the third wrapper 353 may be made of a general filter wrapping paper. For example, the second wrapper 352 and the third wrapper 353 may be porous wrapping paper or non-porous wrapping paper.

For example, the porosity of the second wrapper 352 may be 35000 CU, but is not limited thereto. In addition, the thickness of the second wrapper 352 may be in the range of 70 um to 80 um, and preferably 78 um. In addition, the basis weight of the second wrapper 352 may be in the range of 20 $g/m^2$ to 25 $g/m^2$, and preferably 23.5 $g/m^2$.

For example, the porosity of the third wrapper 353 may be 24000 CU, but is not limited thereto. In addition, the thickness of the third wrapper 353 may be in the range of 60 um to 70 um, and preferably 68 um. In addition, the basis weight of the third wrapper 353 may be in the range of 20 $g/m^2$ to 25 $g/m^2$, and preferably 21 $g/m^2$.

The fourth wrapper 354 may be made of a polylactic acid (PLA) laminated paper. Here, the polylactic acid (PLA) laminated paper may be a three-layer paper including a paper layer, a polylactic acid (PLA) layer and a paper layer. For example, the thickness of the fourth wrapper 354 may be in the range of 100 um to 120 um, and preferably 110 um. In addition, the basis weight of the fourth wrapper 354 may be in the range of 80 $g/m^2$ to 100 $g/m^2$, and preferably 88 $g/m^2$.

The fifth wrapper 355 may be made of a sterile paper. Here, the sterile paper refers to a paper specially manufactured to improve tensile strength, water resistance, smoothness, and the like, compared with ordinary paper. For example, the basis weight of the fifth wrapper 355 may be in the range of 57 $g/m^2$ to 63 $g/m^2$, and preferably 60 $g/m^2$. In addition, the thickness of the fifth wrapper 355 may be in the range of 64 um to 70 um, and preferably 67 um.

The fifth wrapper 355 may have a predetermined material added therein. Here, silicon may be an example of the predetermined material, but is not limited thereto. For example, silicone has characteristics such as heat resistance with little change with temperature, oxidation resistance, resistance to various chemicals, water repellency, and electrical insulation. However, even if it is not silicon, any material having the above-described properties may be applied (or coated) to the fifth wrapper 355 without limitation.

The front-end plug 33 may be made of cellulose acetate. As an example, the front-plug 33 may be manufactured by adding a plasticizer (e.g., triacetin) to cellulose acetate tow. The mono denier of the filaments constituting the cellulose acetate tow may be in the range of 1.0 to 10.0, and preferably in the range of 4.0 to 6.0. More preferably, the mono denier of the filament of the front-end plug 33 may be 5.0. In addition, the cross-section of the filament constituting the front-end plug 33 may be Y-shaped. The total denier of the front-end plug 33 may be in the range of 20000 to 30000, and preferably in the range of 25000 to 30000. More preferably, the total denier of the front-end plug 33 may be 28000.

In addition, as necessary, the front-end plug 33 may include at least one channel, and the cross-sectional shape of the channel may be manufactured in various shapes.

The cigarette rod 31 may correspond to the cigarette rod 21 described above referring to FIG. 4. Therefore, hereinafter, detailed description of the cigarette rod 31 is omitted.

The first segment 321 may be made of cellulose acetate. For example, the first segment may be a tube-shaped structure containing a hollow therein. The first segment 321 may be manufactured by adding the plasticizer (e.g., triacetin) to the cellulose acetate tow. For example, the mono denier and total denier of the first segment 321 may be the same as the mono and total denier of the front-end plug 33.

The second segment 322 may be made of cellulose acetate. The mono denier of the filaments constituting the second segment 322 may be in the range of 1.0 to 10.0, and preferably may be in the range of 8.0 to 10.0. More preferably, the mono denier of the filament of the second segment 322 may be 9.0. In addition, the cross-section of the filament of the second segment 322 may be Y-shaped. The total denier of the second segment 322 may be in the range of 20000 to 30000, and preferably 25000.

Figure 5:
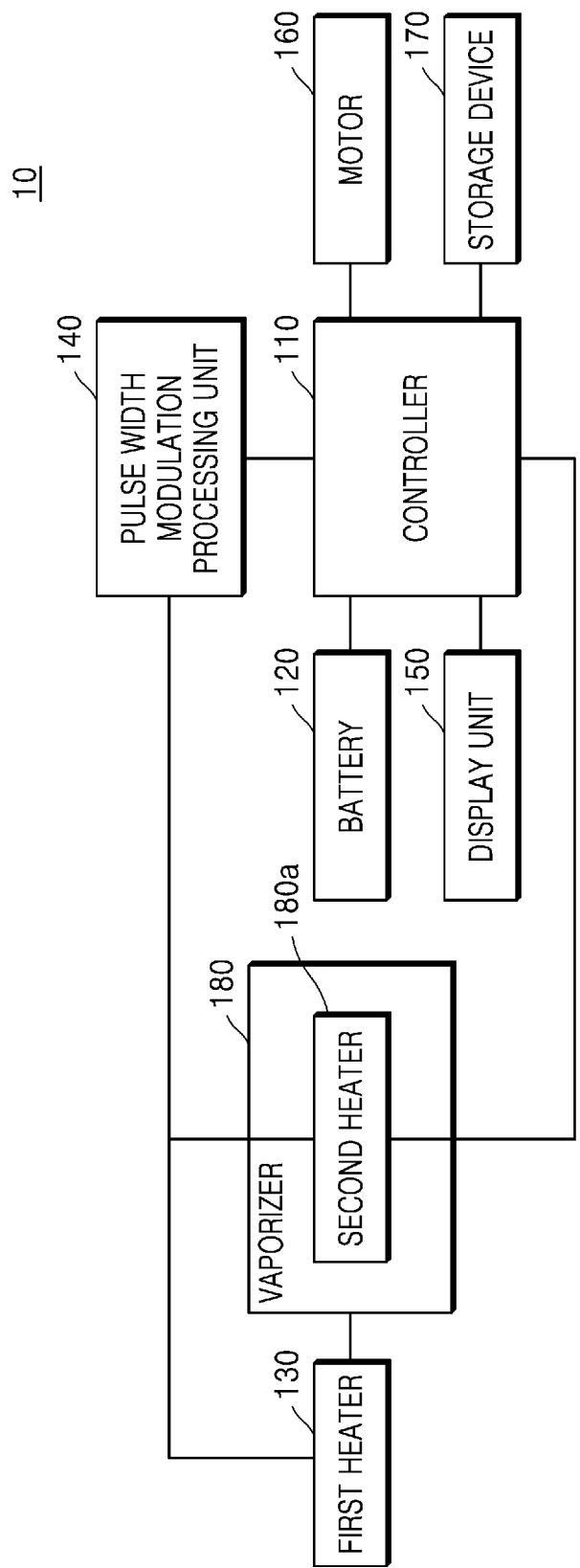
FIG. 5 is a block diagram schematically showing an example of the aerosol generating device according to the present disclosure.

FIG. 5 is a block diagram schematically showing an example of the aerosol generating device according to the present disclosure.

Referring to FIG. 5, the aerosol generating device 10 according to the embodiment may include the controller 110, the battery 120, the first heater 130, a pulse width modulation processing unit 140, a display unit 150, a motor 160, a storage device 170, and a vaporizer 180. Hereinafter, the first heater 130 of FIG. 5 is considered to have the same configuration as the heater 130 described in FIGS. 1 and 2. In addition, for convenience of description, the general function of each component included in the aerosol generating device 10 will be described first, and secondly, the operation of the controller 110 according to the embodiment will be described in detail.

The controller 110 generates and transmits a control signal to control overall operations of the battery 120, the heater 130, the pulse width modulation processing unit 140, the display unit 150, the motor 160, the storage device 170, and the vaporizer 180 included in the aerosol generating device 10. Although not shown in FIG. 5, according to an embodiment, the controller 110 may further include an input receiving unit (not shown) that receives a user's button input or touch input, and a communication unit (not shown) capable of communicating with an external communication device such as a user terminal. In addition, although not shown in FIG. 5, the controller 110 may further include a module for performing proportional-integral-differential (PID) control on the first heater 130.

The battery 120 supplies power to the heater 130, and the level of the power supplied to the heater 130 may be adjusted by a control signal generated by the controller 110. According to an embodiment, a regulator that keeps the voltage of the battery at a constant level may be included between the controller 110 and the battery 120.

The heater 130 generates heat by specific resistance when a current is applied, and when the aerosol generating substrate is contacted (combined) with the heated heater 130, aerosols may be generated.

The pulse width modulation processing unit 140 transmits a pulse width modulation (PWM) signal to the heater 130 so that the controller 110 may control power supplied to the first heater 130 and the second heater 180a using the PWM signal. Depending on the embodiment, the pulse width modulation processing unit 140 may be included in the controller 110, and a PWM signal output from the pulse width modulation processing unit 140 may be a digital PWM signal.

The display unit 150 visually outputs various alarm messages generated by the aerosol generating device 10 so that a user using the aerosol generating device 10 may check the alarm. The user may check the battery power shortage message or the heater overheat warning message output to the display unit 150, and stop the operation of the aerosol generating device 10 or take appropriate measures before the aerosol generating device 10 is damaged.

The controller 110 may drive the motor 160 so that the user may recognize through the tactile sense that the aerosol generating device 10 is ready to be used.

The storage device 170 stores various information for controller 110 to appropriately control the power supplied to the first heater 130 and the second heater 180a so that a consistent flavor may be provided to a user who uses the aerosol generating device 10. The storage device 170 may include not only a non-volatile memory such as a flash memory, but also a volatile memory that temporarily stores data while power is being supplied.

The vaporizer 180 may generate aerosol by heating the liquid composition, and the generated aerosol may be transferred to the user through the cigarette 200. As described referring to FIGS. 1 and 2, the vaporizer 180 may include the liquid storage unit, the liquid delivery means, and the heating element. In particular, the vaporizer 180 may include the heating elements for heating the liquid composition stored in the liquid storage unit. In FIG. 5, the heating element for heating the liquid composition is shown as the second heater 180a. The liquid storage unit may be manufactured to be detachable from or attached to the vaporizer 180, or may be manufactured as one body with the vaporizer 180.

The controller 110, the pulse width modulation processing unit 140, the display unit 150, the storage device 170, and the vaporizer 180 according to an embodiment of the present disclosure may correspond to at least one or more processors or may include at least one or more processors. Accordingly, the controller 110, the pulse width modulation processing unit 140, the display unit 150, the storage device 170 and the vaporizer 180 may be driven in a form included in other hardware devices, such as a microprocessor or a general purpose computer system.

Hereinafter, a process in which the aerosol generating device 10 operates will be described according to embodiments.

The aerosol generating device 10 according to FIG. 5 may include the first heater 130 for heating the cigarette inserted in a first portion of the aerosol generating device 10, the second heater 180a that heats a liquid composition stored in a cartridge detachably attached to a second portion of the aerosol generating device 10, and the controller 110 controlling power supplied to the first heater 130 and the second heater 180a. Herein, the controller 110 may control power supplied to the second heater 180a based on a heating pattern of the first heater 130. In detail, the pulse width modulation processing unit 140 may generate and transmit the PWM signal based on the signal transmitted from the controller 110, and the first heater 130 and the second heater 180a may be supplied with power according to the PWM signal.

Figure 4:
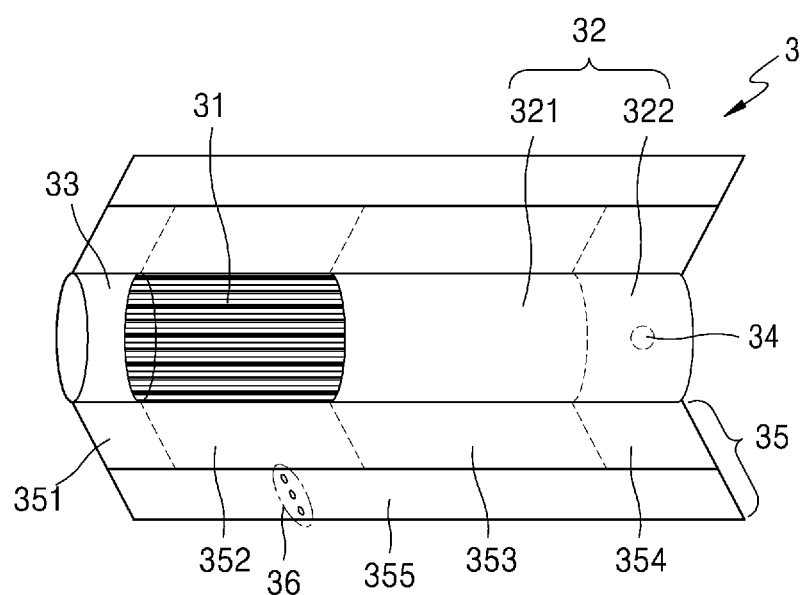

First, the first portion is where the cigarette described in FIGS. 3 and 4 is inserted. When the cigarette is inserted into the first portion, the heat energy of the first heater 130 is transferred to the cigarette, thereby generating the aerosol according to the aerosol generating substrate contained in the cigarette. The second portion may correspond to the position where the vaporizer 180 described in FIGS. 1 and 2 is detachably attached. When the liquid composition stored in the cartridge of the vaporizer 180 is exhausted, the user may temporarily detach the vaporizer 180 located in the second portion of the aerosol generating device 10 or the cartridge included in the vaporizer 180, and then re-attach the vaporizer 180 or the cartridge filled with the liquid composition to the second portion.

According to the present disclosure, in controlling the power supplied to the second heater 180a, the controller 110 controls the power supply of the second heater 180a based on the heating pattern of the first heater 130. As such, it is possible to provide a stable amount of vapor to the user compared with when controlling the power supply of the second heater 180a without considering the heating pattern of the first heater 130. When the first heater 130 supplied with power under the control of the controller 110 is heated, the temperature inside the aerosol generating device 10 rises according to the specific thermal conductivity and specific heat of the material of the aerosol-generating device 10. This internal temperature rise also affects the temperature rise of the second heater 180a. According to the present disclosure, the controller 110 may identify the temperature rise inside the aerosol generating device 10 according to the heating pattern of the first heater 130, and may supply an appropriate power to the second heater 180a. Through the appropriate power supply, the second heater 180a may sufficiently heat the liquid composition of the cartridge.

In an embodiment, the heating pattern of the first heater 130 identified by the controller 110 may be a pattern in which the first heater 130 reaches a pre-set preheating temperature and maintains the preheating temperature for a pre-set period of time. For example, in the case where the first heater 130 reaches the preheating target temperature of 260° C. and the target temperature is maintained for 3 seconds, the controller 110 generates a power signal based on the heating pattern of the first heater 130 and sends the power signal to the second heater 180a through the pulse width modulation processing unit 140. Here, the power signal for the second heater 180a, which corresponds to the heating pattern of the first heater 130, may be generated based on information previously stored in the controller 110 or information stored in the storage device 170 connected to the controller 110 by wired or wireless connection.

In another embodiment, the heating pattern of the first heater 130 identified by the controller 110 may be a pattern in which the first heater 130 reaches the pre-set preheating temperature and maintains the preheating temperature for a pre-set period of time, which results in the internal temperature of the aerosol generating device 10 measured by the temperature sensor exceeding a pre-set value. In this embodiment, the controller 110 may detect through a temperature sensor that an internal temperature of the aerosol generating device 10 rises as the first heater 130 is heated, and may control power supplied to the second heater 180a based on whether the detected temperature exceeds a pre-set value.

In particular, according to the present embodiment, the controller 110 may determine whether the first heater 130 reaches the pre-set preheating temperature and maintains the preheating temperature for a pre-set period of time (primary determination), and determines whether the internal temperature of the aerosol generating device 10 exceeds a pre-set value as the first heater 130 is heated (secondary determination). Through this two-step determination procedure, the controller 110 may finely control the power to be supplied to the second heater 180a. In the present embodiment, as an example of measuring the internal temperature of the aerosol generating device 10, the temperature sensor may be attached to the cartridge in which the liquid composition is stored, and according to an embodiment, at least one temperature sensor may be attached inside the aerosol generating device 10.

In another embodiment, the heating pattern identified by the controller 110 may be a pattern in which the internal temperature of the aerosol generating device 10 exceeds a pre-set value after the first heater 130 reaches a pre-set preheating temperature. In this case, the controller 110 may perform reduction control of power supplied to the second heater based on the heating pattern.

Figure 6:
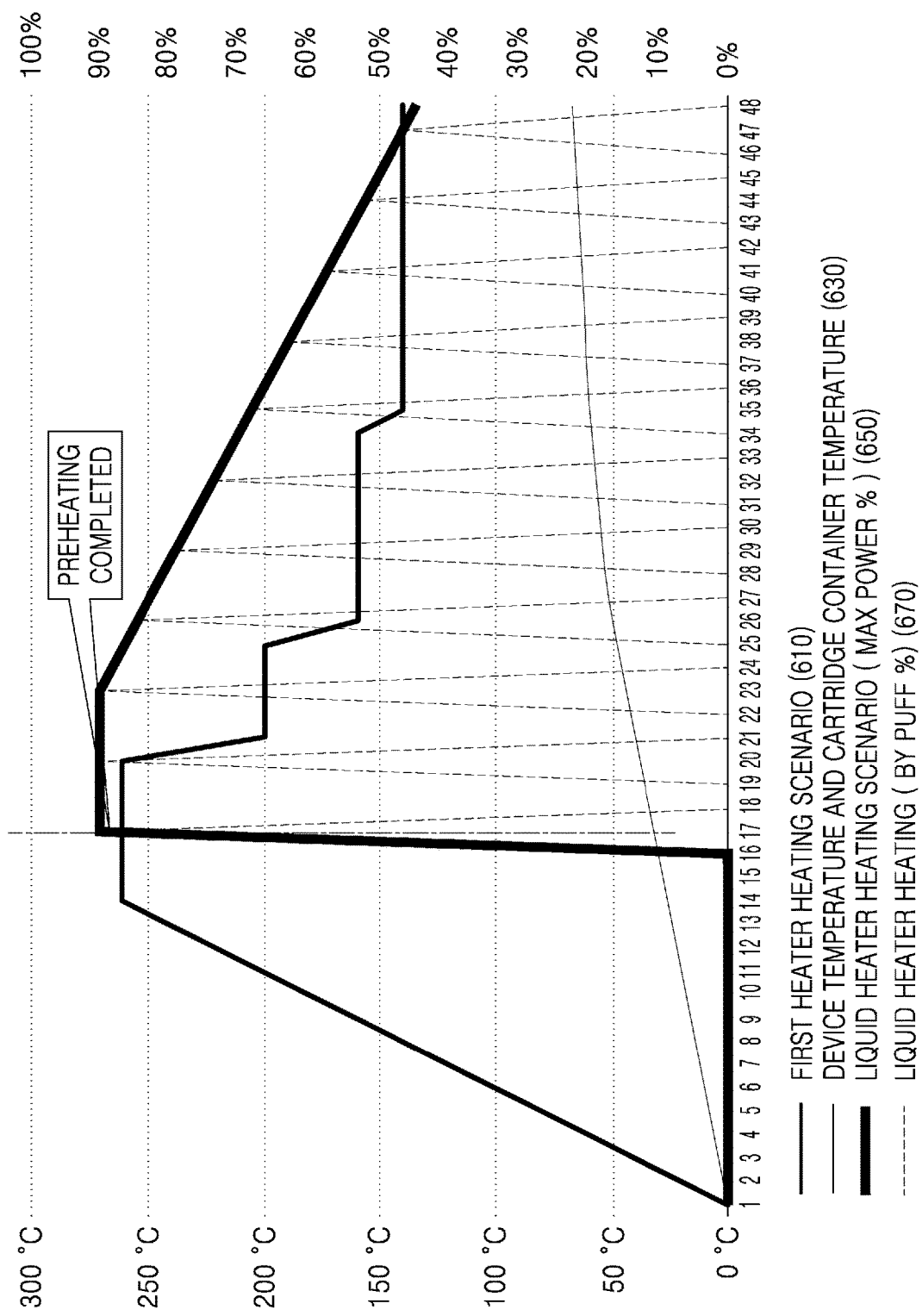
FIG. 6 is a diagram for explaining a process in which a controller controls reduction of the power supplied to a second heater.

FIG. 6 is a diagram for explaining a process in which the controller controls reduction of the power supplied to the second heater.

FIG. 6 shows a graph of a first heater heating scenario 610, a device temperature and a cartridge container temperature 630, a liquid heater heating maximum power scenario 650, and a liquid heater power scenario 670 according to a puff In FIG. 6, the graphs of the first heater heating scenario 610 and the device temperature and the cartridge container temperature 630 are to be interpreted with the temperature axis on the left, and the graphs of the liquid heater heating maximum power scenario 650 and the liquid heater power scenario 670 according to the puff are to be interpreted with the percent power axis on the right.

First, according to the first heater heating scenario 610, the first heater 130 at room temperature may reach the preheating target temperature of 260° C., and then maintain the preheating target temperature for about 3 seconds, thereby completing preheating. After the preheating is completed, the first heater 130 gradually lowers in a stepwise manner the temperature of the first heater 130 to heat the aerosol generating substrate contained in the cigarette.

According to the graph of the device temperature and the cartridge container temperature 630, it may be seen that as the first heater 130 is heated, the device temperature and the cartridge container temperature also gradually increase over time. After the device temperature and the cartridge container temperature 630 reach about 50° C. at a time point of about 27 seconds, the temperature gradually rises while the temperature rising slope decreases. As described above, when the device temperature and the cartridge container temperature 630 rise, energy required for vaporization of the liquid composition may decrease. That is, as the device temperature and the cartridge container temperature 630 increase, it is preferable that the power of the second heater 180a is reduced by the controller 110. If the power supplied to the second heater 180a is not reduced by the controller 110, the flavor of the aerosol may be changed as the liquid composition is excessively vaporized, thereby degrading the user's smoking satisfaction. In FIG. 6, for convenience of description, the device temperature and the cartridge container temperature are written together, but depending on the embodiment, only one of the device temperature and the cartridge container temperature may be adopted.

The graph of the liquid heater heating maximum power scenario 650 is a graph showing the maximum amount of power supplied to the liquid heater, and the amount of power supplied to the second heater 180a may gradually decrease over time in inverse proportion to the rise of the device temperature and the cartridge container temperature 630.

The graph of the liquid heater power scenario 670 according to the puff is a graph showing in detail the change in the amount of power, not the maximum value of the amount of power, supplied to the liquid heater. The graph reflects the fluctuation of the amount of power supplied to the second heater 180a according to the user's puff and elapse of time, and shows that the maximum value of the amount of power in each puff is bounded by the graph of the liquid heater heating maximum power scenario 650.

Unlike the above-described embodiment, the controller 110 may not identify the internal temperature of the aerosol generating device through the temperature sensor, and may use the value obtained by referring to a table for the temperature rise value of the aerosol generating device 10. According to the present exemplary embodiment, without having to additionally include a temperature sensor in the aerosol generating device 10, when the temperature rise value of the first heater 130 becomes a specific value, the internal temperature of the aerosol generating device may be obtained according to the experimental values, by referring to the table stored in advance based on the temperature rise value.

TABLE 1

| Examples | Temperature of the first heater | Holding time | Estimated internal temperature of the aerosol-generating device |
|---|---|---|---|
| 1 | 260° C. | 3 seconds | 30° C. |
| 2 | 200° C. | 3 seconds | 40° C. |
| 3 | 160° C. | 8 seconds | 55° C. |

Table 1 shows an example of a table referenced by the controller 110. When the temperature of the first heater is maintained for more than 3 seconds while reaching 260° C., the controller 110 may estimate the internal temperature of the aerosol generating device to 30° C., and reduce power to be supplied to the second heater 180a according to the estimated temperature. When the temperature of the first heater is maintained for more than 3 seconds at 200° C., the controller 110 may estimate the internal temperature of the aerosol generating device to be 40° C., and control the reduced power to be supplied to the second heater 180a according to the estimated temperature. The estimated temperature of the first heater, the holding time, and the internal temperature of the aerosol generating device listed in Table 1 may vary according to embodiments. In addition, according to an embodiment, the controller 110 may control reduction of the power supplied to the second heater 180a based only on the temperature of the first heater and the estimated internal temperature of the aerosol generating device, or may control reduction of the power supplied to the second heater 180a in proportion to the rise of the internal temperature of the aerosol generating device when the first heater 130 reaches the pre-set preheating temperature. By reducing power supplied to the second heater 180a according to the internal temperature of the aerosol generating device raised by the first heater 130 heating the cigarette as shown in Table 1, the reduction of energy required for the second heater 180a to heat the liquid can be offset. As such, the amount of the aerosol generated by heating of the second heater 180a may be accurately adjusted.

In another embodiment, after the first heater 130 reaches a pre-set preheating temperature, and the reached preheating temperature is maintained for a pre-set period of time, the controller 110 may increase the power supplied to the second heater based on the heat energy transferred to the cigarette heated by the first heater 130.

Figure 7:
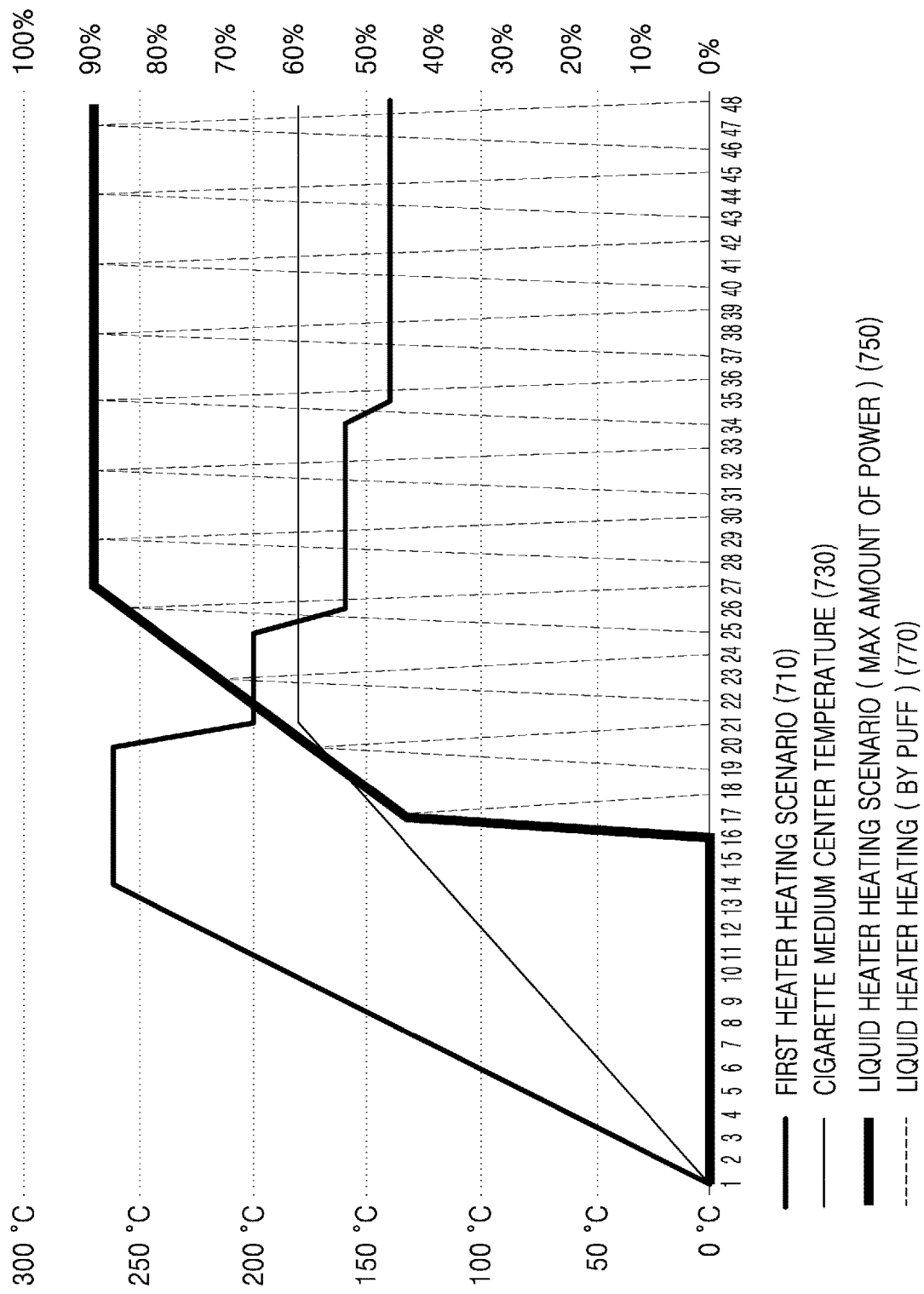
FIG. 7 is a diagram for explaining a process in which a controller increases the power supplied to a second heater.

FIG. 7 is a diagram for explaining a process in which the controller increases the power supplied to the second heater.

FIG. 7 shows a graph of a first heater heating scenario 710, a cigarette medium center temperature 730, a liquid heater heating maximum power scenario 750, and a liquid heater power scenario 770 according to the puff. In FIG. 7, the graphs of the first heater heating scenario 710 and the cigarette media center temperature 730 are to be interpreted with the temperature axis on the left, and the graphs of the liquid heater heating maximum power scenario 750 and the liquid heater power scenario 770 according to the puff are to be interpreted with the percent power axis on the right. Hereinafter, the medium and the aerosol generating substrate are considered synonymous.

First, according to the first heater heating scenario 710, the first heater 130 at room temperature reaches the preheating target temperature of 260° C., and then maintains the preheating target temperature for about 3 seconds, thereby completing preheating. After the preheating is completed, the first heater 130 heats the medium contained in the cigarette while gradually lowering in a stepwise manner the temperature of the first heater 130.

According to the graph of the cigarette medium center temperature 730, the temperature in the center of the medium of the cigarette rises at a constant slope until about 21 seconds after the first heater 130 starts to heat, and thereafter, the temperature in the center of the medium is maintained. As an example, the controller 110 may obtain a total of heat energy transferred to a cigarette by taking an integral value of a graph of the cigarette medium center temperature 730.

According to the graph of the liquid heater heating maximum power scenario 750, the second heater 180a starts to heat from a time point when about 16 seconds have elapsed since the first heater 130 started to heat. When about 17 seconds have passed after the first heater 130 started to heat, the maximum amount of power supplied to the second heater 180a increases with a constant slope. Here, a time point at which about 17 seconds have elapsed since the first heater 130 started to heat is when the controller 110 increases the power supplied to the second heater 180a.

The graph of the liquid heater electric power scenario 770 according to the puff is a graph illustrating in detail not only the maximum value of the amount of power supplied to the liquid heater, but also the change in the amount of power over time. The graph reflects the fluctuation of the amount of power supplied to the second heater 180a according to the user's puff and the elapse of time, and shows that the maximum value of the amount of power in each puff is bounded by the graph of the liquid heater heating maximum power scenario 750.

If the first heater 130 is heated for a long time, the taste of the medium of the cigarette 20000 gets thick. If the taste of the medium gets thicker, the amount of vapor needs to be increased accordingly to provide a consistent smoking feeling to the user. Since the aerosol that the user inhales through the aerosol generating device is the sum of the aerosol generated as each of the first heater 130 and the second heater 180a is heated, in order to provide the user with the same level of satisfaction with smoking each time, it is necessary to increase the atomization amount by the second heater 180a in proportion to the concentration level of the aerosol getting higher as the cigarette is heated by the first heater 130. The present exemplary embodiment described through FIG. 7 satisfies the need as described above.

As a preferred embodiment of the present disclosure, when the first heater reaches the pre-set preheating temperature, the controller 110 may reduce the power supplied to the second heater 180a in proportion to the rise of the internal temperature of the aerosol generating device, and then may increase the power supplied to the second heater 180a based on the heat energy transferred to the cigarette.

Figure 8:
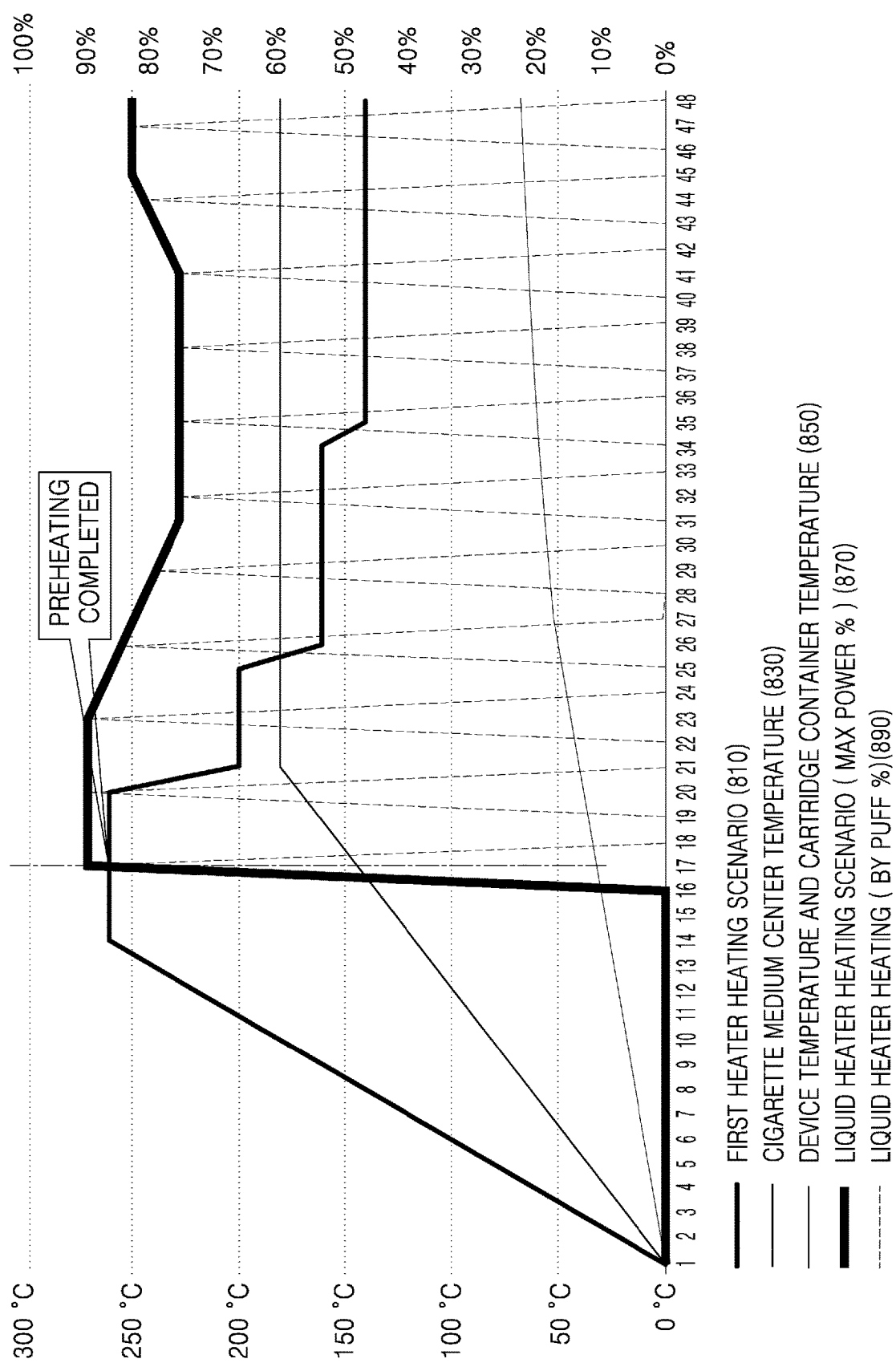
FIG. 8 is a diagram for explaining a process of increasing the power again after a controller reduces the power supplied to a second heater.

FIG. 8 is a diagram for explaining a process of increasing the power again after the controller reduces the power supplied to the second heater.

FIG. 8 shows a graph of a first heater heating scenario 810, a cigarette medium center temperature 830, a cartridge container temperature 850, a liquid heater heating maximum power scenario 870, and a liquid heater power scenario 890 according to the puff. In FIG. 8, the graphs of the first heater heating scenario 810, the cigarette media center temperature 830, and the cartridge container temperature 850 are to be interpreted along the temperature axis on the left, and the graphs of the liquid heater heating maximum power scenario 870 and the liquid heater power scenario 890 according to the puff are to be interpreted along the percent power axis on the right.

FIG. 8 is a diagram for explaining an embodiment combining the embodiments described in FIGS. 6 and 7. When the first heater 130 reaches a preheating target temperature of 260° C. and the reached temperature is maintained for a period of time, the controller 110 may consider that the first heater 130 satisfies the heating pattern, and may obtain the temperature of the aerosol generating device elevated in the process of heating the first heater 130. The controller 110 may start reducing the power supplied to the second heater 180a at about 23 seconds in inverse proportion to the temperature rise of the aerosol generating device, and then may increase the amount of power supplied to the second heater 180a by a certain amount at about 41 seconds according to the graph of the cigarette media center temperature 830.

By controlling the power supplied to the first heater 130 and the second heater 180a of the aerosol generating device according to the graph shown in FIG. 8, it is possible to solve the problem that an incorrect amount of power is supplied to the second heater 180a when the internal temperature of the aerosol-generating device is increased by the first heater 130. Also, it is possible to prevent the deterioration of the smoking feeling that occurs when the temperature in the center of the cigarette medium by the first heater 130 is maintained high. In FIG. 8, the heating temperature of the first heater and the second heater, and the time points of 23 seconds and 41 seconds at which the power supplied to the second heater 180a is changed are examples, and may be varied according to embodiments.

As another embodiment, when the first heater 130 is heated according to the heating pattern, the controller 110 may control power supplied to the second heater 180a based on a temperature profile corresponding to the heating pattern. Here, the temperature profile may be stored in the controller 110 or the storage device 170. Also, the temperature profile may include analog or digital information on a scenario of reducing or increasing power supplied to the second heater 180a according to a heating pattern of the first heater 130.

FIG. 9 is a flowchart illustrating an example of a method of controlling the power of the first and the second heaters in the aerosol generating device according to the present disclosure.

The method according to FIG. 9 may be implemented by the aerosol generating device 10 according to FIG. 5, and thus will be described with reference to FIG. 5. Hereinafter, descriptions overlapping with those described in FIG. 5 will be omitted.

The first heater 130 may heat the cigarette inserted into the first portion of the aerosol generating device 10 (S910).

The second heater 180a may heat the liquid composition stored in the cartridge attached to the second portion of the aerosol generating device 10 (S920).

The controller 110 identifies the heating pattern by which the first heater 130 is heated (S930), and determines whether the heating pattern matches a pre-set pattern (S940).

When the heating pattern matches the pre-set pattern, the controller 110 may reduce or increase the power supplied to the second heater 180a according to the heating pattern (S950)

The present disclosure relates to the aerosol generating device including the first heater for heating the cigarette and the second heater for heating the liquid, and a method of operation of the aerosol generating device. In the aerosol generating device according to the present disclosure, power supplied to the second heater is determined based on the heating pattern of the first heater. Therefore, when the user smokes using the aerosol generating device according to the present disclosure, a more consistent and satisfactory smoking experience may be achieved than when using the conventional externally heated aerosol generating device.

One or more embodiments described above may be implemented in the form of a computer program that may be executed on a computer through various components, and such a computer program may be recorded in a computer-readable recording medium. At this time, the computer-readable recording medium may be a magnetic medium (e.g., a hard disk, a floppy disk, and a magnetic tape), an optical recording medium (e.g., a CD-ROM and a DVD), a magneto-optical medium (e.g., a floptical disk), and a hardware device specifically configured to store and execute program instructions (e.g., a ROM, a RAM, and a flash memory).

Meanwhile, the computer program recorded on the medium may be specially designed and configured for example embodiments or may be published and available to one of ordinary skill in computer software. Examples of computer programs include machine language code such as code generated by a compiler, as well as high-level language code that may be executed by a computer using an interpreter or the like.

Specific implementations described in one or more embodiments are examples, and do not limit the scope of one or more embodiments in any way. For brevity of description, descriptions of conventional electronic components, control systems, software, and other functional aspects of the systems may be omitted. Furthermore, the connecting lines, or connectors shown in the various figures presented are intended to represent exemplary functional relationships and/or physical or logical couplings between the various elements, and it should be noted that many alternative or additional functional relationships, physical connections or circuit connections may be present in a practical device. Moreover, no item or component is essential to the practice of one or more embodiments unless the element is specifically described as "essential" or "critical".

The use of the terms "a" and "an" and "the" and similar referents in the context of describing one or more embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. One or more embodiments are not limited to the described order of the steps. The use of any and all examples, or exemplary language (e.g., "such as") provided herein, is intended merely to better illuminate the present disclosure and does not pose a limitation on the scope of one or more embodiments unless otherwise claimed. Numerous modifications and adaptations will be readily apparent to one of ordinary skill in the art without departing from the spirit and scope of one or more embodiments.

INDUSTRIAL APPLICABILITY

One embodiment according to the present disclosure may be utilized to manufacture a next-generation electronic cigarette that improves the function of a conventional electronic cigarette.

What is claimed is:

1. An aerosol generating device comprising:
a first heater configured to heat a cigarette inserted into a first portion of the aerosol generating device;
a second heater configured to heat a liquid composition stored in a cartridge that is detachably attached to a second portion of the aerosol generating device; and
a controller configured to control power supplied to the first heater and the second heater,
wherein the controller controls power supplied to the second heater based on a heating pattern by which the first heater is heated.

2. The aerosol generating device of claim 1, wherein the heating pattern indicates that the first heater reaches a pre-set preheating temperature and maintains the preheating temperature for a pre-set period of time.

3. The aerosol generating device of claim 2, wherein the heating pattern indicates that an internal temperature of the aerosol generating device measured by a temperature sensor exceeds a pre-set value as the first heater maintains the preheating temperature for the pre-set period of time.

4. The aerosol generating device of claim 1, wherein
the heating pattern indicates that an internal temperature of the aerosol generating device exceeds a pre-set value after the first heater reaches a pre-set preheating temperature, and
the controller reduces the power supplied to the second heater based on the heating pattern.

5. The aerosol generating device of claim 4, wherein the internal temperature of the aerosol generating device is measured by a temperature sensor attached to the cartridge.

6. The aerosol generating device of claim 4, wherein the internal temperature of the aerosol generating device is obtained by referring to a table showing different periods of time for maintaining the pre-set preheating temperature and different temperatures of the aerosol generating device which respectively correspond to the different periods of time.

7. The aerosol generating device of claim 1, wherein the controller increases the power supplied to the second heater based on heat energy transferred to the cigarette when a pre-set preheating temperature is maintained for a pre-set period of time after the first heater reaches the pre-set preheating temperature.

8. The aerosol generating device of claim 1, wherein the controller reduces the power supplied to the second heater in proportion to a rise of an internal temperature of the aerosol generating device when the first heater reaches a pre-set preheating temperature.

9. The aerosol generating device of claim 8, wherein the controller increases the reduced the power supplied to the second heater, based on heat energy transferred to the cigarette.

10. The aerosol generating device of claim 1, wherein the controller stores a temperature profile corresponding to the heating pattern, and controls the power supplied to the second heater according to the stored temperature profile.

11. A method of controlling power of a first heater and a second heater in an aerosol generating device, the method comprising:
   heating, by the first heater, a cigarette inserted into a first portion of the aerosol generating device;
   heating, by the second heater, a liquid composition stored in a cartridge detachably attached to a second portion of the aerosol generating device; and
   controlling, by a controller, power supplied to the second heater based on a heating pattern by which the first heater is heated.

12. The method of claim 11, wherein the heating pattern indicates that the first heater reaches a pre-set preheating temperature and maintains the preheating temperature for a pre-set period of time.

13. The method of claim 12, wherein the heating pattern indicates that an internal temperature of the aerosol generating device measured by a temperature sensor exceeds a pre-set value as the first heater maintains the preheating temperature for the pre-set period of time.

14. The method of claim 11, wherein
   the heating pattern indicates that an internal temperature of the aerosol generating device exceeds a pre-set value after the first heater reaches a pre-set preheating temperature, and
   the controlling includes reducing the power supplied to the second heater based on the heating pattern.

15. The method of claim 14, wherein the internal temperature of the aerosol generating device is measured by a temperature sensor attached to the cartridge.

16. The method of claim 14, wherein the internal temperature of the aerosol generating device is obtained by referring to a table showing different periods of time for maintaining the pre-set preheating temperatures and different temperatures of the aerosol generating device which respectively correspond to the different periods of time.

17. The method of claim 11, wherein the controlling includes increasing the power supplied to the second heater based on heat energy transferred to the cigarette when a pre-set preheating temperature is maintained for a pre-set period of time after the first heater reaches the pre-set preheating temperature.

18. The method of claim 11, wherein the controlling includes reducing the power supplied to the second heater in proportion to a rise of an internal temperature of the aerosol generating device when the first heater reaches a pre-set preheating temperature.

19. The method of claim 18, wherein the controlling includes increasing the reduced power supplied to the second heater based on heat energy transferred to the cigarette.

20. The method of claim 11, wherein the controlling includes storing a temperature profile corresponding to the heating pattern, and controlling the power supplied to the second heater according to the stored temperature profile.

* * * * *